United States Patent
Kuramoto et al.

(10) Patent No.: US 8,969,591 B2
(45) Date of Patent: Mar. 3, 2015

(54) METHOD FOR PRODUCING CYCLIC SULFONIC ACID ESTER AND INTERMEDIATE THEREOF

(71) Applicant: Wako Pure Chemical Industries, Ltd., Osaka (JP)

(72) Inventors: Ayako Kuramoto, Kawagoe (JP); Kuniaki Okamoto, Kawagoe (JP); Tsutomu Watahiki, Kawagoe (JP); Motoshige Sumino, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 14/163,682

(22) Filed: Jan. 24, 2014

(65) Prior Publication Data

US 2014/0142324 A1    May 22, 2014

Related U.S. Application Data

(63) Continuation of application No. 13/388,405, filed as application No. PCT/JP2010/063062 on Aug. 3, 2010, now Pat. No. 8,673,963.

(30) Foreign Application Priority Data

Aug. 4, 2009 (JP) ................. 2009-181963

(51) Int. Cl.
*C07D 327/10* (2006.01)
*C07D 327/04* (2006.01)

(52) U.S. Cl.
CPC ............ *C07D 327/04* (2013.01); *C07D 327/10* (2013.01)
USPC ........................................................ 549/40

(58) Field of Classification Search
CPC ..................................................... C07D 327/10
USPC ........................................................ 549/40
See application file for complete search history.

(56) References Cited

U.S. PATENT DOCUMENTS 3,100,779 A    8/1963 Mannheimer
5,807,847 A    9/1998 Thatcher et al.

FOREIGN PATENT DOCUMENTS

| JP | 2000-511197 | 8/2000 |
| JP | 2002-329528 | 11/2002 |
| JP | 2006-4813 | 1/2006 |
| KR | 10-2007-0101716 | 10/2007 |

OTHER PUBLICATIONS

Bonini, B.F. et al., "Synthesis of 1-Alkene-1,3-Sultones from 2,3-Epoxy-Alkanesulfonyl Chlorides," Synlett (12), p. 1411-1413 (1998).
Morikawa, F. et al., "Contact Hypersensitivity and Sensitizing Mechanism of the Sultones Contaminated I nAlkyl Ethoxy Sulfate Products," Japanese Journal of Allergology, 27(7), p. 648-661 (1978).
Creary, X., "Reactions of Pivaloin Derivatives with Lithium Tetramethylpiperidide," J. Org. Chem., 45(12), p. 2419-2425 (1980).
Roberts, D.W. et al., "Electrophilic Reactions of Skin-Sensitizing Sultones," Chem. Res. Toxicol., 20(1), p. 61-71 (2007).
Kaz'Mina, N.B. et al., "Reaction of hexafluorobutadiene with sulfur trioxide," Izv. Akad. Nauk SSSR Ser. Khim., (1) p. 118-126 (1979).
Lee, A.W.M. et al., "Synthesis and Diels-Alder reactions of α,(β-unsaturated, γ-sultone," Chem. Commun., p. 611-612 (1997).
Karsh, S. et al., "Ring Closing Metathesis in the Synthesis of Sultones and Sultams," Synthesis (10), p. 1696-1712 (2004).
Jiang et al.: "Synthesis and Diels-Alder Reactions of Prop-l-ene-1,3-soltone, and Chemical Transformations of the Diels-Alder Adducts"; Tetrahedron, Elsevier Science Publishers, Amsterdam, NL, vol. 55, No. 8, Feb. 19, 1999, pp. 2245-2262 52835.

*Primary Examiner* — Taofiq A Solola
(74) *Attorney, Agent, or Firm* — Hamre, Schumann, Mueller & Larson, P.C.

(57) ABSTRACT

The present invention is directed to provide an efficient production method which is capable of not only obtaining a cyclic sulfonic acid ester (sultone) at low cost and in high yield, but also the sulfonic acid ester (sultone) stably even in a commercial scale. The present invention relates to a method for producing hydroxysultone comprising a first step where a diol having a specified structure and a thionyl halide are reacted to obtain a cyclic sulfite having a specified structure, and a second step where the cyclic sulfite is reacted with water or/and alcohol; a method for producing an unsaturated sultone having a specified structure comprising a third step where a hydroxylsultone having a specified structure is reacted with an acid halide or an acid anhydride to obtain an intermediate, subsequently the intermediate is treated with a base; as well as a cyclic sulfite having a specified structure.

7 Claims, No Drawings

METHOD FOR PRODUCING CYCLIC SULFONIC ACID ESTER AND INTERMEDIATE THEREOF

TECHNICAL FILED

The present invention relates to a method for producing a cyclic sulfonic acid ester (sultone) which is useful, for example, as an additive to non-aqueous electrolyte in a lithium ion secondary battery or the like. In more detail, the present invention relates to an efficient method for producing a cyclic sulfonic acid ester (sultone) using dihydroxysulfonate as a raw material.

BACKGROUND OF THE INVENTION

It has been known that a cyclic sulfonic acid ester (sultone) is a useful compound, for example, as an additive to non-aqueous electrolyte in a lithium ion secondary battery, which is capable of improving various battery characteristics. Specifically, it has been known that, for example, by adding an unsaturated sultone such as 1,3-propenesultone to non-aqueous electrolyte, not only an effect to suppress reductive decomposition reaction of electrolyte on a negative electrode can be expected, but also decrease of battery capacity in high-temperature storage test and cycle test can be suppressed, and gas generation associated with decomposition of electrolyte can be also suppressed (see, for example, Patent Literature 1 and the like). In addition, it has been also known that non-aqueous electrolyte containing, for example, hydroxysultone such as hydroxypropanesultone provides an effect to suppress decrease of charge and discharge efficiency which is significant in a lithium ion secondary battery, prolongation of cycle life, and an effect to suppress decrease of battery capacity (see, for example, Patent Literature 2, and the like).

As a method for producing an unsaturated sultone such as 1,3-propenesultone which is a kind of such cyclic sulfonic acid ester (sultone), specifically, for example, (1) a method where sodium allylsulfonate obtained by reacting allyl bromide and sodium sulfite is brominated to obtain dibromoderivative thereof, subsequently cyclization reaction is carried out under acidic condition to obtain 2-bromo-1,3-propanesultone, thereafter dehydrobromination reaction is carried out to obtain the 1,3-propenesultone (see, for example, Non-Patent Literature 1 and the like), (2) a method where allylsulfonyl chloride obtained by reacting sodium allylsulfonate and phosphorous oxychloride is reacted with 1,3-dibromo-5,5-dimethylhydantoin to obtain 2-bromo-1,3-propanesultone, thereafter dehydrobromination reaction is carried out to obtain the 1,3-propenesultone (see, for example, Non-Patent Literature 2 and the like), (3) a method where 1,3-propanesultone is reacted with a halogenating agent in the presence of a radical initiator to obtain halogenated 1,3-propanesultone, thereafter dehydrohalogenation reaction is carried out to obtain the 1,3-propenesultone (see, for example, Patent Literature 3 and the like), (4) a method where allyl vinylsulfonic acid ester obtained by reacting vinylsulfonyl chloride and allyl alcohol is subjected to ring-closing metathesis in the presence of a ruthenium catalyst to obtain the 1,3-propenesultone (see, for example, Non-Patent Literature 3 and the like), and the like, have been known.

In addition, as a method for producing hydroxysultone such as 2-hydroxy-1,3-propanesultone, specifically, for example, (5) a method where sodium hydrogen sulfite prepared from sodium metabisulfite and sodium hydroxide is reacted with epichlorohydrin to obtain sodium 3-chloro-2-hydroxypropanesulfite, which is thereafter subjected to ring-closing reaction under heat condition to obtain the 1,3-propenesultone has been described (see, for example, Patent Literature 4 and the like).

However, in the above-described method (1), there are such problems that since all of bromine used to obtain 1,3-propenesultone become a waste, atom efficiency is poor, and that the step of dehydrobromination reaction carried out under a reduced pressure shows a low yield, and the like. When the present inventors actually implemented the method (1) in a commercial scale, 1,3-propenesultone as the target could not be obtained at all. Though detail is not clear, since the dehydrobromination reaction is carried out without using a solvent at a high temperature, it is considered that decomposition or gelation rather than the ring-closing reaction might occur in a commercial scale. In the above-described method (2), there are such problems that a substantial amount of expensive 1,3-dibromo-5,5-dimethylhydantoin has to be used, as well as that yield is low, and the like. In addition, in the above-described method (3), there are such problems that in the halogenation reaction of 1,3-propanesultone, 3-halogeno-1,3-propanesultone which is different in halogen substitution site is formed as a by-product, and since the 3-halogeno-1,3-propanesultone is not dehydrohalogenated and 1,3-propanesultone as the target is not formed, yield cannot be improved, and the like. Furthermore, in the above-described method (4), a comparatively expensive ruthenium catalyst has to be used, and hence the method can be hardly said as a commercial method.

In addition, when the present inventors traced the above-described method (5) disclosed as a method for producing 2-hydroxy-1,3-propanesultone, 2-hydroxy-1,3-propanesultone could not be obtained at all and presence of sodium 3-chloro-2-hydroxypropanesulfite as a synthetic intermediate could not also be identified. As a result of the study by the present inventors, it was found that sodium 3-chloro-2-hydroxypropanesulfonate instead of sodium 3-chloro-2-hydroxypropanesulfite had been formed. Thus, either methods have such problems that yield is low; a substantial amount of the comparatively expensive reagent has to be used; a cyclic sulfonic acid ester (sultone) as the target is difficult to obtain stably in a commercial scale; and the like, and are not necessarily advantageous method.

In such a circumstance, development of an efficient method for producing a cyclic sulfonic acid ester (sultone) as the target which is capable of not only using an economical raw material and a reagent but also synthesizing stably even in an commercial scale has been demanded.

PRIOR ART LITERATURES

Patent Literatures

Patent Literature 1: JP-A-2002-329528
Patent Literature 2: JP-A-2006-4813
Patent Literature 3: KR-A-1020070101716
Patent Literature 4: U.S. Pat. No. 3,100,779

Non-Patent Literatures

Non-Patent Literature 1: Chem. Commun, 1997, 611
Non-Patent Literature 2: Synlett 1998, 1411
Non-Patent Literature 3: Synthesis 2004, 10, 1696

DISCLOSURE OF INVENTION

Problem to be Solved by the Invention

The problem to be solved by the present invention is to provide an efficient method for producing a cyclic sulfonic acid ester (sultone) as the target which is capable of not only obtaining at low cost in high yield, but also obtaining the cyclic sulfonic acid ester (sultone) stably even in a commercial scale.

Means for Solving the Problem

An aspect of the present invention is a method for producing a compound represented by the general formula [1]:

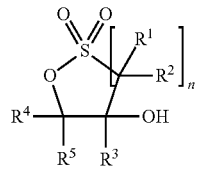

[1]

(wherein n pieces of $R^1$, n pieces of $R^2$, $R^3$, $R^4$ and $R^5$ represent each independently a hydrogen atom or a C1-3 alkyl group, and n represents an integer of 1 or 2) comprising a first step where a compound represented by the general formula [2]:

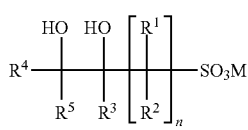

[2]

(wherein n pieces of $R^1$, n pieces of $R^2$, $R^3$, $R^4$ and $R^5$ and n are same as above, and M represents an alkali metal atom) and a thionyl halide are reacted to obtain a compound represented by the general formula [3]:

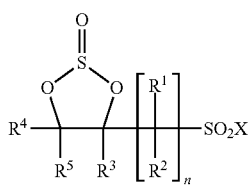

[3]

(wherein X represents a halogen atom, and n pieces of $R^1$, n pieces of $R^2$, $R^3$, $R^4$ and $R^5$ and n are same as above); and a second step where the aforementioned compound represented by the general formula [3] is reacted with water or/and alcohol.

In addition, another aspect of the present invention is a method for producing a compound represented by the general formula [4]:

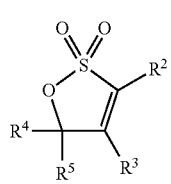

[4]

(wherein $R^2$, $R^3$, $R^4$ and $R^5$ represent each independently a hydrogen atom or a C1-3 alkyl group) comprising a third step where a compound represented by the general formula [1']:

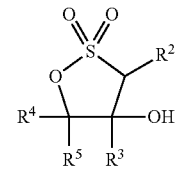

[1']

(wherein $R^2$, $R^3$, $R^4$ and $R^5$ are same as above) is reacted with an acid halide or an acid anhydride to obtain a compound represented by the general formula [5]:

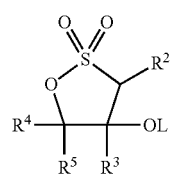

[5]

(wherein L represents a leaving group derived from the aforementioned acid halide or acid anhydride, and $R^2$, $R^3$, $R^4$ and $R^5$ are same as above), subsequently the compound represented by the aforementioned general formula [5] is treated with a base.

Further, another aspect of the present invention is a compound represented by the above-described general formula [3].

Effect of the Invention

According to the production method of the present invention, not only a cyclic sulfonic acid ester (sultone) as the target such as a hydroxylsultone represented by the general formula [1] and an unsaturated sultone represented by the general formula [4] can be obtained in high yield, but also production of the cyclic sulfonic acid ester (sultone) with a stable yield even in a commercial scale can be realized. In addition, even when the above-described first step and second step, or the above-described first step, second step and third step are carried out continuously in one-pot reaction, production of the above-described hydroxysultone represented by the general formula [1] and the above-described unsaturated sultone represented by the general formula [4] in high efficiency can be realized.

BEST MODE FOR CARRYING-OUT OF THE INVENTION

The C1-3 alkyl group represented by $R^1$ in the general formulas [1], [2] and [3] as well as $R^2$, $R^3$, $R^4$ and $R^5$ in the general formulas [1], [1'], [2], [3], [4] and [5] may be either linear or branched one. Specifically, the C1-3 alkyl group includes, for example, a methyl group, an ethyl group, a n-propyl group, an isopropyl group, and the like, and among them, a methyl group of C1 alkyl group is preferable.

The alkali metal atom represented by M in the general formula [2] includes, for example, a lithium atom, a sodium atom, a potassium atom, a rubidium atom, a cesium atom, and the like. Among them, a lithium atom, a sodium atom and a potassium atom are preferable, and further a sodium atom is more preferable.

The halogen atom represented by X in the general formula [3] includes, for example, a fluorine atom, a chlorine atom, a bromine atom, an iodine atom, and the like. Among them, a chlorine atom is preferable.

As n in the general formulas [1], [2] and [3], 1 is preferable.

The leaving group derived from acid halide or acid anhydride represented by L in the general formula [5] includes C1-6 alkylsulfonyl group which is optionally substituted by a halogen atom, C6-10 arylsulfonyl group, C2-7 alkylcarbonyl group (acyl group) which is optionally substituted by a halogen atom, C7-11 arylcarbonyl group, and the like. Specifically, the leaving group includes C1-6 alkylsulfonyl group which is optionally substituted by a halogen atom such as, for example, a methanesulfonyl group, an ethanesulfonyl group, a n-propanesulfonyl group, an isopropanesulfonyl group, a n-butanesulfonyl group, an isobutanesulfonyl group, a sec-butanesulfonyl group, a tert-butanesulfonyl group, a cyclobutanesulfonyl group, a n-pentanesulfonyl group, an isopentanesulfonyl group, a sec-pentanesulfonyl group, a tert-pentanesulfonyl group, a neopentanesulfonyl group, a 2-methylbutanesulfonyl group, a 1,2-dimethylpropanesulfonyl group, a 1-ethylpropanesulfonyl group, a cyclopentanesulfonyl group, a n-hexanesulfonyl group, an isohexanesulfonyl group, a sec-hexanesulfonyl group, a tert-hexanesulfonyl group, a neohexanesulfonyl group, a 2-methylpentanesulfonyl group, a 1,2-dimethylbutanesulfonyl group, a 2,3-dimethylbutanesulfonyl group, a 1-ethylbutanesulfonyl group, a cyclohexanesulfonyl group, and a trifluoromethanesulfonyl group; C6-10 arylsulfonyl group such as, for example, a benzenesulfonyl group, an o-toluenesulfonyl group, a m-toluenesulfonyl group, a p-toluenesulfonyl group, a 2,3-xylenesulfonyl group, a 2,4-xylenesulfonyl group, a 2,5-xylenesulfonyl group, a 2,6-xylenesulfonyl group, a 3,4-xylenesulfonyl group, a 3,5-xylenesulfonyl group, a 1-naphthalenesulfonyl group, and a 2-naphthalenesulfonyl group; C2-7 alkylcarbonyl group which is optionally substituted by a halogen atom such as, for example, a methylcarbonyl group (an acetyl group), an ethylcarbonyl group, a n-propylcarbonyl group, an isopropylcarbonyl group, a n-butylcarbonyl group, an isobutylcarbonyl group, a sec-butylcarbonyl group, a tert-butylcarbonyl group, a cyclobutylcarbonyl group, a n-pentylcarbonyl group, an isopentylcarbonyl group, a sec-pentylcarbonyl group, a tert-pentylcarbonyl group, a neopentylcarbonyl group, a 2-methylbutylcarbonyl group, a 1,2-dimethylpropylcarbonyl group, a 1-ethylpropylcarbonyl group, a cyclopentylcarbonyl group, a n-hexylcarbonyl group, an isohexylcarbonyl group, a sec-hexylcarbonyl group, a tert-hexylcarbonyl group, a neohexylcarbonyl group, a 2-methylpentylcarbonyl group, a 1,2-dimethylbutylcarbonyl group, a 2,3-dimethylbutylcarbonyl group, a 1-ethylbutylcarbonyl group, a cyclohexylcarbonyl group, and a trifluoromethylcarbonyl group (a trifluoroacetyl group); and C7-11 arylcarbonyl group such as, for example, a phenylcarbonyl group (a benzoyl group), an o-tolylcarbonyl group, a m-tolylcarbonyl group, a p-tolylcarbonyl group, a 2,3-xylylcarbonyl group, a 2,4-xylylcarbonyl group, a 2,5-xylylcarbonyl group, a 2,6-xylylcarbonyl group, a 3,4-xylylcarbonyl group, a 3,5-xylylcarbonyl group, a 1-naphthylcarbonyl group and a 2-naphthylcarbonyl group. Among them, a methanesulfonyl group, a p-toluenesulfonyl group, a trifluoromethanesulfonyl group, a methylcarbonyl group (an acetyl group), a trifluoromethylcarbonyl group (a trifluoroacetyl group), a phenylcarbonyl group (a benzoyl group) are preferable, and further a methanesulfonyl group and a methylcarbonyl group (an acetyl group) are more preferable.

As $R^1$ in the general formulas [1], [2] and [3], as well as $R^2$, $R^3$, $R^4$ and $R^5$ in the general formulas [1], [1'], [2], [3], [4] and [5], a hydrogen atom is preferable.

A preferred specific example of the compound represented by the above-described general formulas [1], [2] and [3] includes a compound where $R^1$ is a hydrogen atom and n is 1 in the general formulas [1], [2] and [3]. More specifically, a preferred specific example of the compound represented by the general formula [2] includes a compound represented by the general formula [2']:

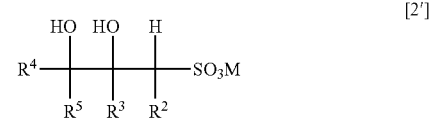

(wherein $R^2$, $R^3$, $R^4$, $R^5$ and M are same as above); a preferred specific example of the compound represented by the general formula [3] includes a compound represented by the general formula [3']:

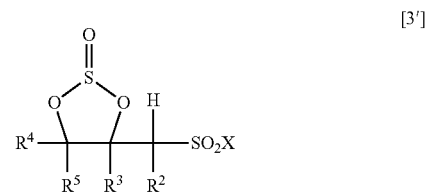

(wherein $R^2$, $R^3$, $R^4$, $R^5$ and X are same as above); and a preferred specific example of the compound represented by the general formula [1] includes a compound represented by the above-described general formula [1']. The compound represented by the general formula [2'] and the compound represented by the general formula [3'] are useful as intermediates for obtaining not only a saturated sultone such as the compound represented by the general formula [1'] (hydroxysultone), but also a compound represented by the general formula [4] (unsaturated sultone) in high yield as well as with high selectivity. Therefore, the production method of the present invention is a preferable production method as a method for obtaining a compound represented by the above-described general formula [1'] (hydroxysultone) and a compound represented by the above-described general formula [4] (unsaturated sultone).

More preferred specific examples of the compounds represented by the above-described general formulas [1] to [5] include compounds where all of $R^1$, $R^2$, $R^3$, $R^4$ and $R^5$ in the general formulas [1] to [5] are each a hydrogen atom, and n is 1 in the general formulas [1], [2] and [3]. More specifically, a more preferred example of the compound represented by the general formula [2] includes a compound represented by the general formula [2"]:

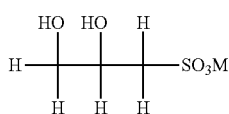

(wherein M is same as above); a more preferred example of the compound represented by the general formula [3] includes a compound represented by the general formula [3"]:

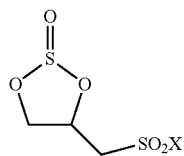

(wherein X is same as above); a more preferred example of the compound represented by the general formulas [1] and [1'] includes a compound represented by the formula [1"]:

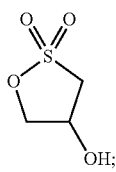

a more preferred example of the compound represented by the general formula [5] includes a compound represented by the general formula [5']:

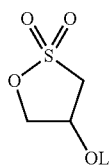

(wherein L is same as above); a more preferred example of the compound represented by the general formula [4] includes a compound represented by the formula [4']:

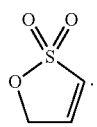

The compound represented by the above formula [1"] (2-hydroxy-1,3-propanesultone) and the compound represented by the above formula [4'] (1,3-propenesultone) are preferable compounds as an additive to non-aqueous electrolyte in a lithium ion secondary battery. That is, the present invention is a more preferable production method as a method for obtaining the compound represented by the above formula [1"] (2-hydroxy-1,3-propanesultone) and the compound represented by the above formula [4'] (1,3-propenesultone). In addition, the compounds represented by the above-described general formulas [2"], [3"] and [5'] are more preferable compounds as intermediates of the sultones.

In the production method of the present invention, the compound represented by the above-described general formula [1] (hydroxysultone) can be synthesized by reacting a compound represented by the above-described general formula [2] (a diol) with a predetermined amount of a thionyl halide to the compound (the diol) to obtain a compound represented by the above-described general formula [3] (cyclic sulfite) (a first step), and reacting the cyclic sulfite with water or/and an alcohol (a second step). Further, the compound represented by the above-described general formula [4] (unsaturated sultone) can be synthesized by reacting the compound represented by the above-described general formula [1'] (hydroxysultone) which is obtained by the above-described first step and second step with a predetermined amount of acid halide or acid anhydride to the compound (hydroxysultone) to obtain a compound represented by the above-described general formula [5], subsequently treating the compound with a base (a third step). In addition, by carrying out the above-described first step and second step continuously, that is, in one-pot reaction, the compound represented by the general formula [1] (hydroxysultone) can be obtained in higher yield as well as with higher efficiency compared with the case where the above-described first step and second step are carried out stepwise. Furthermore, by carrying out not only the above-described first step and second step, but also the third step continuously, that is, in one-pot reaction, the compound represented by the general formula [4] (unsaturated sultone) can be further more efficiently obtained compared with the case where these steps are carried out stepwise.

As the compound represented by the general formula [2] to be used in the present invention, that is, as the diol represented by the general formula [2], a commercially available one or a synthesized one by a usual method may be appropriately used. The usual method includes a method where an alkali metal salt of alkenylsulfonic acid such as sodium allylsulfonate and sodium homoallylsulfonate is epoxidized, thereafter hydrolysis reaction is carried out, and the like. In addition, in the present invention, in particular, as the diol represented by the general formula [2], a diol wherein all of $R^1$, $R^2$, $R^3$, $R^4$ and $R^5$ in the general formula [2] are each a hydrogen atom as well as n is 1, that is, an alkali metal salt of 2,3-dihydroxypropanesulfonic acid is preferably used.

As the thionyl halide to be reacted with the diol represented by the general formula [2] in the above-described first step, a commercially available one may be sufficiently used. Specifically, the thionyl halide includes, for example, thionyl chloride, thionyl bromide, thionyl iodide, and the like, and among them, thionyl chloride is preferable from the viewpoint that it is economical and the handling is easy. In addition, amount of thionyl halide to be used is usually 1.6 to 20 equivalents, and preferably 1.8 to 10 equivalents relative to the diol represented by the general formula [2]. It should be noted that as for these thionyl halides, one kind may be used alone or plural kinds may be used in combination.

The above-described first step may be carried out in the absence of solvent or in an organic solvent. The solvent is not particularly limited, so long as the organic solvent does not react with the diol represented by the general formula [2] as a raw material of the reaction. Specifically, for example, hexane, benzene, toluene, dichloromethane, dichloroethane, chloroform, carbon tetrachloride, diethyl ether, diisopropyl ether, tetrahydrofuran (THF), ethyl acetate, dimethyl carbonate, acetonitrile, dioxane, and the like are preferably used. In addition, amount of the organic solvent to be used is not particularly limited, but, for example, usually 0.1 to 20 mL, and preferably 0.2 to 10 mL relative to 1 mmol of the diol represented by the general formula [2]. It should be noted that as for these organic solvents, one kind may be used alone or plural kinds may be used in combination.

The above-described first step may be carried out in the presence of a catalyst which is capable of promoting the reaction. The catalyst includes N,N-disubstituted amide such as, for example, N,N-dimethylformamide and N-methyl-N-phenylformamide; tertiary amine such as, for example, triethylamine and N,N-diethylaniline; nitrogen-containing heterocyclic compound such as, for example, pyridine, 4-ethylpyridine, 2-methyl-5-ethylpyridine and 4-(N,N-dimethylamino)pyridine (DMAP); and the like. In addition, amount of the catalyst to be used is not particularly limited, but, for example, usually 0.001 to 20 equivalents, preferably 0.01 to 10 equivalents, and more preferably 0.01 to 5 equivalents relative to the diol represented by the general formula [2]. It should be noted that as for these catalysts, one kind may be used alone or plural kinds may be used in combination.

Reaction temperature in the above-described first step may be set at a temperature at which the reaction of the diol represented by the general formula [2] and the thionyl halide proceeds, and the temperature is preferably set at a temperature at which the diol and the thionyl halide react efficiently and the compound represented by the above-described general formula [3], that is, the cyclic sulfite represented by the above-described general formula [3] can be efficiently synthesized. Specifically, the reaction temperature is, for example, usually −20° C. to 100° C., and preferably 0° C. to 80° C.

Reaction time in the above-described first step is hard to say, because it may vary depending on amount of the thionyl halide to be used relative to the diol represented by the general formula [2], kind of organic solvent and amount thereof to be used, reaction temperature, and the like, but it is set in a range of usually 0.2 to 24 hours, and preferably 0.5 to 12 hours.

In the above-described first step, a method for isolating the cyclic sulfite represented by the general formula [3], which is a product of the first step, from the solution after completion of the reaction may be a common post-treatment operation. Specifically, the product can be isolated, for example, by pouring the reaction solution into cool water after completion of the reaction, subsequently extracting the mixture with an appropriate organic solvent such as toluene, thereafter washing appropriately the resultant extract with water or the like, and concentrating the solution after washing. It should be noted that besides the isolation operation as described above, a purification operation such as recrystallization and column chromatography may be added thereto. In addition, in the present invention, since the desired compound represented by the general formula [1], that is, the hydroxysultone represented by the general formula [1] can be obtained in high yield as well as high-efficiently by carrying out the above-described first step and the second step to be described later continuously, when improvements in yield and efficiency are further desired, it is desirable to carry out the second step without carrying out the post-treatment operation after completion of the above-described first step.

The cyclic sulfite represented by the general formula [3] obtained in such way is, as described above, an important synthetic intermediate for synthesizing the hydroxysultone represented by the general formula [1] and the compound represented by the general formula [4], that is, the unsaturated sultone represented by the general formula [4].

The above-described second step is a step where the cyclic sulfite represented by the general formula [3] and water or/and alcohol are reacted. Amount of the water or/and alcohol to be used (total amount when plural kinds are used in combination) is usually 0.8 to 20 equivalents, preferably 1.8 to 10 equivalents, and more preferably 1.8 to 7 equivalents relative to the cyclic sulfite represented by the general formula [3]. As the alcohol, a commercially available one may be used. Specifically, the alcohol includes, for example, methanol, ethanol, n-propanol, isopropanol, n-butanol, isobutanol, sec-butanol, tert-butanol, cyclobutanol, and the like, and among them, methanol and ethanol are preferable. It should be noted that as for these water or/and alcohol, one kind may be used alone or plural kinds may be used in combination.

In the above-described second step, preferably an acid is used to promote the reaction. Specifically, the acid includes inorganic acid such as, for example, hydrochloric acid, nitric acid, sulfuric acid and phosphoric acid; and organic acid such as, for example, carbonic acid, acetic acid, methanesulfonic acid and p-toluenesulfonic acid. Among them, hydrochloric acid is preferable. In addition, amount of the acid to be used is usually 0.8 to 10 equivalents, and preferably 1 to 5 equivalents relative to the cyclic sulfite represented by the general formula [3]. It should be noted that as for these acids, one kind may be used alone or plural kinds may be used in combination. In addition, when the above-described first step and second step are carried out continuously in one-pot reaction, since the acid component derived from the thionyl halide used in the above-described first step acts as an acid, the acid has not necessarily to be added.

In the above-described second step, since the water or/and alcohol double as a reaction solvent, another organic solvent is not necessarily required, but the second step may be carried out by using an organic solvent in combination. The organic solvent is not particularly limited, so long as the organic solvent does not react with the cyclic sulfite represented by the general formula [3] as a raw material of the reaction. Specifically, the organic solvent includes, for example, hexane, benzene, toluene, dichloromethane, dichloroethane, chloroform, carbon tetrachloride, diethyl ether, diisopropyl ether, tetrahydrofuran (THF), ethyl acetate, dimethyl carbonate, acetonitrile, dioxane, N,N-dimethylformamide, dimethylsulfoxide, and the like. In addition, amount of the organic solvent to be used is not particularly limited, but, for example, usually 0.02 to 10 mL, and preferably 0.05 to 5 mL. It should be noted that as for these organic solvents, one kind may be used alone or plural kinds may be used in combination.

Reaction temperature in the above-described second step may be set at a temperature at which the reaction of the cyclic sulfite represented by the general formula [3] and water or/and alcohol proceeds, and the temperature is preferably set at a temperature at which the cyclic sulfite and water or/and alcohol react efficiently and the hydroxysultone represented by the above-described general formula [1] can be synthesized in high yield. Specifically, the reaction temperature is, for example, usually −20° C. to 100° C., preferably 0° C. to 60° C., and more preferably 10° C. to 30° C.

Reaction time in the above-described second step is hard to say, because it may vary depending on amount of water or/and alcohol to be used relative to the cyclic sulfite represented by the general formula [3], kind of acid and amount thereof to be used, reaction temperature, and the like, but it is set in a range of usually 0.1 to 6 hours, and preferably 0.2 to 3 hours.

In the above-described second step, a method for isolating and purifying the hydroxysultone represented by the general formula [1], which is a product of the second step, from the solution after completion of the reaction may be a common post-treatment and purification operations. Specifically, the product can be efficiently purified, for example, by concentrating the reaction solution after completion of the reaction, subsequently adding an appropriate organic solvent such as ethyl acetate and water, if necessary, to the concentrated residue and stirring, then removing the aqueous layer, washing the resultant organic layer with water or the like, concentrating the solution after washing, then adding an appropriate organic solvent such as toluene to the concentrated residue to precipitate crystal, and filtering the formed crystal. It should be noted that instead of the purification operation as described above, a purification operation by usual column chromatography may be carried out. In addition, in the present invention, since the desired unsaturated sultone represented by the general formula [4] can be obtained further high-efficiently by carrying out not only the above-described first step and second step but also even the third step described later continuously, when improvements in efficiency is further desired, it is desirable to carry out the third step without carrying out the post-treatment operation after completion of the above-described second step.

In the above-described third step, as the acid halide or acid anhydride to be reacted with the hydroxysultone represented by the general formula [1'], a commercially available one can be sufficiently used. Specifically, the acid halide includes, C1-6 alkylsulfonyl halide which is optionally substituted by a halogen atom such as, for example, methanesulfonyl chloride, methanesulfonyl bromide, methanesulfonyl iodide, ethanesulfonyl chloride, ethanesulfonyl bromide, ethanesulfonyl iodide, n-propanesulfonyl chloride, n-propanesulfonyl bromide, n-propanesulfonyl iodide, isopropanesulfonyl chloride, isopropanesulfonyl bromide, isopropanesulfonyl iodide, n-butanesulfonyl chloride, n-butanesulfonyl bromide, n-butanesulfonyl iodide, isobutanesulfonyl chloride, isobutanesulfonyl bromide, isobutanesulfonyl iodide, sec-butanesulfonyl chloride, sec-butanesulfonyl bromide, sec-butanesulfonyl iodide, tert-butanesulfonyl chloride, tert-butanesulfonyl bromide, tert-butanesulfonyl iodide, cyclobutanesulfonyl chloride, cyclobutanesulfonyl bromide, cyclobutanesulfonyl iodide, n-pentanesulfonyl chloride, n-pentanesulfonyl bromide, n-pentanesulfonyl iodide, isopentanesulfonyl chloride, isopentanesulfonyl bromide, isopentanesulfonyl iodide, sec-pentanesulfonyl chloride, sec-pentanesulfonyl bromide, sec-pentanesulfonyl iodide, tert-pentanesulfonyl chloride, tert-pentanesulfonyl bromide, tert-pentanesulfonyl iodide, neopentanesulfonyl chloride, neopentanesulfonyl bromide, neopentanesulfonyl iodide, 2-methylbutanesulfonyl chloride, 2-methylbutanesulfonyl bromide, 2-methylbutanesulfonyl iodide, 1,2-dimethylpropanesulfonyl chloride, 1,2-dimethylpropanesulfonyl bromide, 1,2-dimethylpropanesulfonyl iodide, 1-ethylpropanesulfonyl chloride, 1-ethylpropanesulfonyl bromide, 1-ethylpropanesulfonyl iodide, cyclopentanesulfonyl chloride, cyclopentanesulfonyl bromide, cyclopentanesulfonyl iodide, n-hexanesulfonyl chloride, n-hexanesulfonyl bromide, n-hexanesulfonyl iodide, isohexanesulfonyl chloride, isohexanesulfonyl bromide, isohexanesulfonyl iodide, sec-hexanesulfonyl chloride, sec-hexanesulfonyl bromide, sec-hexanesulfonyl iodide, tert-hexanesulfonyl chloride, tert-hexanesulfonyl bromide, tert-hexanesulfonyl iodide, neohexanesulfonyl chloride, neohexanesulfonyl bromide, neohexanesulfonyl iodide, 2-methylpentanesulfonyl chloride, 2-methylpentanesulfonyl bromide, 2-methylpentanesulfonyl iodide, 1,2-dimethylbutanesulfonyl chloride, 1,2-dimethylbutanesulfonyl bromide, 1,2-dimethylbutanesulfonyl iodide, 2,3-dimethylbutanesulfonyl chloride, 2,3-dimethylbutanesulfonyl bromide, 2,3-dimethylbutanesulfonyl iodide, 1-ethylbutanesulfonyl chloride, 1-ethylbutanesulfonyl bromide, 1-ethylbutanesulfonyl iodide, cyclohexanesulfonyl chloride, cyclohexanesulfonyl bromide, cyclohexanesulfonyl iodide, trifluoromethanesulfonyl chloride, trifluoromethanesulfonyl bromide, and trifluoromethanesulfonyl iodide; C6-10 arylsulfonyl halide such as, for example, benzenesulfonyl chloride, benzenesulfonyl bromide, benzenesulfonyl iodide, o-toluenesulfonyl chloride, o-toluenesulfonyl bromide, o-toluenesulfonyl iodide, m-toluenesulfonyl chloride, m-toluenesulfonyl bromide, m-toluenesulfonyl iodide, p-toluenesulfonyl chloride, p-toluenesulfonyl bromide, p-toluenesulfonyl iodide, 2,3-xylenesulfonyl chloride, 2,3-xylenesulfonyl bromide, 2,3-xylenesulfonyl iodide, 2,4-xylenesulfonyl chloride, 2,4-xylenesulfonyl bromide, 2,4-xylenesulfonyl iodide, 2,5-xylenesulfonyl chloride, 2,5-xylenesulfonyl bromide, 2,5-xylenesulfonyl iodide, 2,6-xylenesulfonyl chloride, 2,6-xylenesulfonyl bromide, 2,6-xylenesulfonyl iodide, 3,4-xylenesulfonyl chloride, 3,4-xylenesulfonyl bromide, 3,4-xylenesulfonyl iodide, 3,5-xylenesulfonyl chloride, 3,5-xylenesulfonyl bromide, 3,5-xylenesulfonyl iodide, 1-naphthalenesulfonyl chloride, 1-naphthalenesulfonyl bromide, 1-naphthalenesulfonyl iodide, 2-naphthalenesulfonyl chloride, 2-naphthalenesulfonyl bromide, and 2-naphthalenesulfonyl iodide; C2-7 alkylcarboxylic halide which is optionally substituted by a halogen atom such as, for example, acetyl chloride, acetyl bromide, acetyl iodide, propionyl chloride (propionic acid chloride), propionyl bromide (propionic acid bromide), propionyl iodide (propionic acid iodide), n-butyryl chloride (butyric acid chloride), n-butyryl bromide (butyric acid bromide), n-butyryl iodide (butyric acid iodide), isobutyryl chloride (isobutyric acid chloride), isobutyryl bromide (isobutyric acid bromide), isobutyryl iodide (isobutyric acid iodide), n-valeryl chloride (valeric acid chloride), n-valeryl bromide (valeric acid bromide), n-valeryl iodide (valeric acid iodide), isovaleryl chloride (isovaleric acid chloride), isovaleryl bromide (isovaleric acid bromide), isovaleryl iodide (isovaleric acid iodide), sec-valeryl chloride (hydrangelic acid chloride), sec-valeryl bromide (hydrangelic acid bromide), sec-valeryl iodide (hydrangelic acid iodide), tert-valeryl chloride (pivalic acid chloride), tert-valeryl bromide (pivalic acid bromide), tert-valeryl iodide (pivalic acid iodide), cyclobutanecarbonyl chloride, cyclobutanecarbonyl bromide, cyclobutanecarbonyl iodide, n-hexanoyl chloride (caproic acid chloride), n-hexanoyl bromide (caproic acid bromide), n-hexanoyl iodide (caproic acid iodide), isohexanoyl chloride, isohexanoyl bromide, isohexanoyl iodide, sec-hexanoyl chloride, sec-hexanoyl bromide, sec-hexanoyl iodide, tert-hexanoyl chloride, tert-hexanoyl bromide, tert-hexanoyl iodide, neohexanoyl chloride, neohexanoyl bromide, neohexanoyl iodide, 2-methylvaleryl chloride, 2-methylvaleryl bromide, 2-methylvaleryl iodide, 1,2-dimethylbutyryl chloride, 1,2-dimethylbutyryl bromide, 1,2-dimethylbutyryl iodide, 1-ethylbutyryl chloride, 1-ethylbutyryl bromide, 1-ethylbutyryl iodide, cyclopentanecarbonyl chloride, cyclopentanecarbonyl bromide, cyclopentanecarbonyl iodide, n-heptanoyl chloride (enanthic acid chloride), n-heptanoyl bromide (enanthic acid bromide), n-heptanoyl iodide (enanthic acid iodide), isoheptanoyl chloride, isoheptanoyl bromide, isoheptanoyl iodide, sec-heptanoyl chloride, sec-heptanoyl bromide, sec-heptanoyl iodide, tert-heptanoyl chloride, tert-heptanoyl bromide, tert-heptanoyl iodide, neoheptanoyl chloride, neoheptanoyl bromide, neoheptanoyl iodide, 2-methylhexanoyl chloride, 2-methylhexanoyl bromide, 2-methylhexanoyl iodide, 1,2-dimethylvaleryl chloride, 1,2-dimethylvaleryl bromide, 1,2-dimethylvaleryl iodide, 2,3-dimethylvaleryl chloride, 2,3-dimethylvaleryl bromide, 2,3-dimethylvaleryl iodide, 1-ethylvaleryl chloride, 1-ethylvaleryl bromide, 1-ethylvaleryl iodide, cyclohexanecarbonyl chloride, cyclohexanecarbonyl bromide, cyclohexanecarbonyl iodide, trifluoroacetyl chloride, trifluoroacetyl bromide, and trifluoroacetyl iodide; C7-11 arylcarboxylic halide such as, for example, benzoyl chloride, benzoyl bromide, benzoyl iodide, o-toluic acid chloride, o-toluic acid bromide, o-toluic acid iodide, m-toluic acid chloride, m-toluic acid bromide, m-toluic acid iodide, p-toluic acid chloride, p-toluic acid bromide, p-toluic acid iodide, 2,3-xylic acid chloride, 2,3-xylic acid bromide, 2,3-xylic acid iodide, 2,4-xylic acid chloride, 2,4-xylic acid bromide, 2,4-xylic acid iodide, 2,5-xylic acid chloride, 2,5-xylic acid bromide, 2,5-xylic acid iodide, 2,6-xylic acid chloride, 2,6-xylic acid bromide, 2,6-xylic acid iodide, 3,4-xylic acid chloride, 3,4-xylic acid bromide, 3,4-xylic acid iodide, 3,5-xylic acid chloride, 3,5-xylic acid bromide, 3,5-xylic acid iodide, 1-naphthoic acid chloride (1-naphthalenecarboxylic acid chloride), 1-naphthoic acid bromide (1-naphthalenecarboxylic acid bromide), 1-naphthoic acid iodide (1-naphthalenecarboxylic acid iodide), 2-naphthoic acid chloride (2-naphthalenecarboxylic acid chloride), 2-naphthoic acid bromide (2-naphthalenecarboxylic acid bromide), and 2-naphthoic acid iodide (2-naphthalenecarboxylic acid iodide); and the like.

In addition, specific example of the above-described acid anhydride includes C2-12 alkylsulfonic anhydride which is optionally substituted by a halogen atom such as, for example, methanesulfonic anhydride, ethanesulfonic anhydride, n-propanesulfonic anhydride, isopropanesulfonic anhydride, n-butanesulfonic anhydride, isobutanesulfonic anhydride, sec-butanesulfonic anhydride, tert-butanesulfonic anhydride, cyclobutanesulfonic anhydride, n-pentanesulfonic anhydride, isopentanesulfonic anhydride, sec-pentanesulfonic anhydride, tert-pentanesulfonic anhydride, neopentanesulfonic anhydride, 2-methylbutanesulfonic anhydride, 1,2-dimethylpropanesulfonic anhydride, 1-ethylpropanesulfonic anhydride, cyclopentanesulfonic anhydride, n-hexanesulfonic anhydride, isohexanesulfonic anhydride, sec-hexanesulfonic anhydride, tert-hexanesulfonic anhydride, neohexanesulfonic anhydride, 2-methylpentanesulfonic anhydride, 1,2-dimethylbutanesulfonic anhydride, 2,3-dimethylbutanesulfonic anhydride, 1-ethylbutanesulfonic anhydride, cyclohexanesulfonic anhydride, and trifluoromethanesulfonic anhydride; C12-20 arylsulfonic anhydride such as, for example, benzenesulfonic anhydride, o-toluenesulfonic anhydride, m-toluenesulfonic anhydride, p-toluenesulfonic anhydride, 2,3-xylenesulfonic anhydride, 2,4-xylenesulfonic anhydride, 2,5-xylenesulfonic anhydride, 2,6-xylenesulfonic anhydride, 3,4-xylenesulfonic anhydride, 3,5-xylenesulfonic anhydride, 1-naphthalenesulfonic anhydride, and 2-naphthalenesulfonic anhydride; C4-14 alkylcarboxylic anhydride which is optionally substituted by a halogen atom such as, for example, acetic anhydride, propanoic acid anhydride (propionic anhydride), n-butanoic acid anhydride (butyric anhydride), isobutanoic acid anhydride (isobutyric anhydride), n-pentanoic acid anhydride (valeric anhydride), isopentanoic acid anhydride (isovaleric anhydride), sec-pentanoic acid anhydride (hydrangelic anhydride), tert-pentanoic acid anhydride (pivalic anhydride), cyclobutanecarboxylic anhydride, n-hexanoic acid anhydride (caproic anhydride), isohexanoic acid anhydride, sec-hexanoic acid anhydride, tert-hexanoic acid anhydride, neohexanoic acid anhydride, 2-methylpentanoic acid anhydride, 1,2-dimethylbutanoic acid anhydride, 1-ethylbutanoic acid anhydride, cyclopentanecarboxylic anhydride, n-heptanoic acid anhydride (enanthic anhydride), isoheptanoic acid anhydride, sec-heptanoic acid anhydride, tert-heptanoic acid anhydride, neoheptanoic acid anhydride, 2-methylhexanoic acid anhydride, 1,2-dimethylpentanoic acid anhydride, 2,3-dimethylpentanoic acid anhydride, 1-ethylpentanoic acid anhydride, cyclohexanecarboxylic anhydride, and trifluoroacetic anhydride; C14-22 arylcarboxylic anhydride such as, for example, benzoic acid anhydride (benzoic anhydride), o-methylbenzoic acid anhydride, m-methylbenzoic acid anhydride, p-methylbenzoic acid anhydride, 2,3-dimethylbenzoic acid anhydride, 2,4-dimethylbenzoic acid anhydride, 2,5-dimethylbenzoic acid anhydride, 2,6-dimethylbenzoic acid anhydride, 3,4-dimethylbenzoic acid anhydride, 3,5-dimethylbenzoic acid anhydride, 1-naphthoic acid anhydride (1-naphthalenecarboxylic anhydride), and 2-naphthoic acid anhydride (2-naphthalenecarboxylic anhydride); and the like.

Among these acid halides or acid anhydrides, acid halide such as methanesulfonyl chloride, methanesulfonyl bromide, trifluoromethanesulfonyl chloride, trifluoromethanesulfonyl bromide, p-toluenesulfonyl chloride, p-toluenesulfonyl bromide, acetyl chloride, acetyl bromide, trifluoroacetyl chloride, trifluoroacetyl bromide, benzoyl chloride, and benzoyl bromide; and acid anhydride such as methanesulfonic anhydride, trifluoromethanesulfonic anhydride, p-toluenesulfonic anhydride, acetic anhydride, trifluoroacetic anhydride, and benzoic acid anhydride (benzoic anhydride) are preferable, and further methanesulfonyl chloride and acetic anhydride are more preferable.

Amount of the above-described acid halide or acid anhydride to be used is usually 0.8 to 10 equivalents, and preferably 1 to 5 equivalents relative to the hydroxysultone represented by the general formula [1']. It should be noted that as for these acid halides or acid anhydrides, one kind may be used alone or plural kinds may be used in combination.

In the reaction in the above-described third step where a compound represented by the general formula [5] is treated with a base to obtain an unsaturated sultone represented by the general formula [4], as the base to be used in the reaction, a commercially available one can be used. Specifically, the base includes tertiary amine such as, for example, triethylamine, pyridine, 1,8-diazabicyclo[5.4.0]undec-7-ene (DBU), and 1,5-diazabicyclo[4.3.0]non-5-ene (DBN); alkali metal salt of carbonic acid such as, for example, sodium carbonate, potassium carbonate, and cesium carbonate; alkali metal halide such as, for example, sodium hydride, and potassium hydride; alkali metal hydroxide such as, for example, sodium hydroxide, and potassium hydroxide; alkali metal alkoxide such as, for example, sodium methoxide, potassium methoxide, sodium ethoxide, potassium ethoxide, lithium tert-butoxide, sodium tert-butoxide, and potassium tert-butoxide; alkyl lithium such as, for example, n-butyl lithium, sec-butyl lithium, tert-butyl lithium, and n-hexyl lithium; metal amide such as, for example, lithium diisopropylamide (LDA), lithium hexamethyldisilazane (LHMDS), sodium hexamethyldisilazane (NaHMDS), and potassium hexamethyldisilazane (KHMDS); and the like. Among them, a comparatively mild base like tertiary amine such as, for example, triethylamine, pyridine, 1,8-diazabicyclo[5.4.0]undec-7-ene (DBU), and 1,5-diazabicyclo[4.3.0]non-5-ene (DBN); alkali metal salt of carbonic acid such as, for example, sodium carbonate, potassium carbonate, and cesium carbonate; and the like is preferable from the viewpoint that the reaction condition is easy to control, and further triethylamine and potassium carbonate are more preferable. In addition, amount of the base to be used may be an amount or more by which the elimination reaction of LO-group in the general formula [5], that is, the double bond formation reaction in the compound represented by the general formula [5] proceeds smoothly.

Specifically, the amount is 0.8 to 20 equivalents, and preferably 1 to 10 equivalents relative to the compound represented by the general formula [5]. It should be noted that as for these bases, one kind may be used alone or plural kinds may be used in combination.

In addition, in the reaction of a hydroxysultone represented by the general formula [1'] and an acid halide or acid anhydride in the above-described third step, when acid halide is used, it is desirable to use a base in the timing of the reaction because hydrogen halide is formed as a by-product. That is, the above-described base can be used not only for the purpose to promote the above-described double bond formation reaction, but also for the purpose to trap the hydrogen halide. It should be noted that even when the base is used in the timing of the reaction with the above-described acid halide or acid anhydride, the above-described specific bases can be used, and amount thereof to be used may be the range in equivalent described above. In addition, when the base is used in the timing of the reaction of a hydroxysultone represented by the general formula [1'] and an acid halide or acid anhydride, sometimes the double bond formation reaction of the compound represented by the general formula [5] proceeds continuously, and an unsaturated sultone represented by the general formula [4] can be obtained, although it depends on an amount of the base to be used.

In the above-described third step, when the base is used in the timing of the reaction of a hydroxysultone represented by the general formula [1'] and an acid halide or acid anhydride, and the base is a liquid, an organic solvent is not necessary used because the base acts as a reaction solvent, but when the base is a solid or the base is not used in the timing of the reaction of a hydroxysultone represented by the general formula [1'] and an acid halide or acid halide or acid anhydride or the like, it is desirable to carry out the reaction in an organic solvent. Such organic solvent is not particularly limited, so long as the organic solvent does not react with the hydroxysultone represented by the general formula [1'] as a raw material of the reaction, the compound represented by the general formula [5], acid halide, acid anhydride, and the like. Specifically, the organic solvent includes, for example, hexane, benzene, toluene, dichloromethane, dichloroethane, chloroform, carbon tetrachloride, diethyl ether, diisopropyl ether, tetrahydrofuran (THF), ethyl acetate, dimethyl carbonate, acetonitrile, dioxane, N,N-dimethylformamide, dimethylsulfoxide, and the like. Among them, hexane, benzene, toluene, dichloromethane, dichloroethane, chloroform, carbon tetrachloride, diethyl ether, diisopropyl ether, tetrahydrofuran (THF), ethyl acetate, dimethyl carbonate and acetonitrile are preferable, and further, ethyl acetate is more preferable. In addition, amount of the organic solvent to be used is not particularly limited, but usually 0.1 to 20 mL, and preferably 0.2 to 10 mL relative to 1 mmol of the hydroxysultone represented by the general formula [1'] or 1 mmol of the compound represented by the general formula [5]. It should be noted that as for these organic solvents, one kind may be used alone or plural kinds may be used in combination, and when the base is a solid and hardly dissolves in the above-described organic solvent, water may be used in combination.

Reaction temperature in the above-described third step may be set at a temperature at which the hydroxysultone represented by the general formula [1'] and the acid halide or acid anhydride can react and the double bond formation reaction of the compound represented by the general formula [5] proceeds, and the temperature is preferably set at a temperature at which the above-described reactions proceed efficiently, and the unsaturated sultone represented by the general formula [4] can be synthesized efficiently. Specifically, the reaction temperature is, for example, usually −40° C. to 70° C., and preferably −30° C. to 50° C.

Reaction time in the above-described third step is hard to say, because it may vary depending on amount of the acid halide or acid anhydride to be used relative to the hydroxysultone represented by the general formula [1'], amount of the base to be used relative to the compound represented by the general formula [5], presence or absence of an organic solvent, kind and amount thereof to be used, reaction temperature, and the like, but it is set in a range of usually 0.1 to 48 hours, and preferably 0.2 to 36 hours. It should be noted that the above-described reaction time represents a total reaction time to synthesize the compound represented by the general formula [4] from the hydroxysultone represented by the general formula [1']. In this total reaction time, the reaction time to synthesize the compound represented by the general formula [5] from the hydroxysultone represented by the general formula [1'] is set in a range of usually 0.05 to 16 hours, and preferably 0.1 to 12 hours, and the reaction time to synthesize the unsaturated sultone represented by the general formula [4] from the compound represented by the general formula [5] is set in a range of usually 0.05 to 32 hours, and preferably 0.1 to 24 hours.

In the above-described third step, a method for isolating the compound represented by the general formula [5] from the solution after completion of the reaction may be a common post-treatment operation. Specifically, the product can be isolated, for example, by adding water to the reaction solution after completion of the reaction, subsequently separating the organic layer, washing the resultant organic layer with saturated sodium bicarbonate aqueous solution and water sequentially, then concentrating the solution after washing. It should be noted that besides the isolation operation as described above, a purification operation such as chromatography may be added thereto. In addition, a method for isolating the unsaturated sultone represented by the general formula [4] from the solution after completion of the reaction may be a common post-treatment operation. Specifically, the unsaturated sultone can be isolated, for example, by adding water to the reaction solution after completion of the reaction, if necessary, subsequently fractionating the organic layer, washing the resultant organic layer with water, then concentrating the solution after washing. Further, when a purification operation is carried out after the isolation, purification can be performed, for example, by adding an appropriate organic solvent such as toluene to the above-described solution after washing or the above-described concentrated residue after concentration, and filtering the crystal formed therein. It should be noted that besides the purification operation as described above, a purification operation such as usual column chromatography may be carried out.

Thus, the present inventors have found out first in the world a method which is capable of producing a hydroxysultone represented by the general formula [1] and an unsaturated sultone represented by the general formula [4] using a diol represented by the general formula [2] which is easy to procure or synthesize as a raw material through a cyclic sulfite represented by the general formula [3] as a synthetic intermediate. This method is a superior production method which is capable of obtaining the desired compound in higher yield, in particular, obtaining the desired compound more efficiently by carrying out these steps continuously in one-pot reaction, compared with the conventional method. In addition, since all of these steps can be carried out under mild conditions, there is little possibility of a trouble such as decomposition and gelation, and the desired compound can be stably obtained even in a commercial scale.

Hereinafter, the present invention will be specifically explained referring to Examples, but the present invention is not limited thereto by any means.

EXAMPLES

Synthetic Example 1

Synthesis of sodium 2,3-dihydroxypropanesulfonate

Reaction Scheme [1]

Sodium sulfite (120 g, 924 mmol, content: 97.0%, produced by Wako Pure Chemical Industries, Ltd.) was dissolved in water (400 mL), and 3-chloro-1,2-propanediol (107.2 g, 970 mmol, produced by Wako Pure Chemical Industries, Ltd.) was added thereto. The solution was refluxed by heating for 1 hour. After completion of the reaction, the reaction solution was concentrated, thereafter methanol (750 mL) was added to the concentrated residue. The crystal formed was filtered, and the resultant crystal was dried, to obtain sodium 2,3-dihydroxypropanesulfonate relevant to the above-described general formula [2] (202.6 g, content: 67.2%, yield: 82.7%) as a white crystal. It should be noted that content of sodium 2,3-dihydroxypropanesulfonate was obtained by $^1$H-NMR using the internal standard method. In addition, it was confirmed that the above-described white crystal contained crystal of sodium chloride as a by-product. Measurement results of $^1$H-NMR are shown below.

$^1$H-NMR (400 MHz, D$_2$O) δ (ppm): 2.97 (2H), 3.54 (2H), 4.05 (1H).

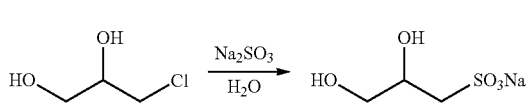

Example 1

Synthesis of 1,3,2-dioxathiolane-2-oxide-4-yl-methanesulfonyl chloride

The First Step, Reaction Scheme [II]

Sodium 2,3-dihydroxypropanesulfonate (80.0 g, 301 mmol, content: 67.2%) divided from the total amount thereof obtained in Synthetic Example 1 was suspended in N,N-dimethylformamide (DMF) (110.3 g, 1509 mmol, produced by Wako Pure Chemical Industries, Ltd.), and the suspension was cooled down to −20° C. to 10° C. Thionyl chloride (107.7 g, 905 mmol, produced by Wako Pure Chemical Industries, Ltd.) was added drop by drop to the cooled suspension, thereafter the suspension was stirred at room temperature for 3 hours to promote the reaction. After completion of the reaction, the reaction solution was added to water (400 mL) which had been cooled to −20° C. to 10° C. Subsequently, toluene (200 mL) was added to this mixture, and the mixture was stirred, and then the organic layer was separated. The separated organic layer was washed with water, thereafter the organic layer was concentrated, to obtain 1,3,2-dioxathiolane-2-oxide-4-yl-methanesulfonyl chloride (65.1 g, yield: 98%) relevant to the above-described general formula [3] as a yellow oil. It should be noted that 1,3,2-dioxathiolane-2-oxide-4-yl-methanesulfonyl chloride was obtained as a mixture of 2 kinds of isomers (isomer A and isomer B). Measurement results of $^1$H-NMR are shown below.

<Isomer A>
$^1$H-NMR (400 MHz, CDCl$_3$) δ (ppm): 3.98 (1H, dd, CH$_2$), 4.12 (1H, dd, CH$_2$), 4.55 (1H, dd, OCH$_2$), 4.96 (1H, dd, OCH$_2$), 5.52 (1H, m, CH).

<Isomer B>
$^1$H-NMR (400 MHz, CDCl$_3$) δ (ppm): 4.25 (1H, dd, CH$_2$), 4.43 (1H, dd, CH$_2$), 4.74 (1H, dd, OCH$_2$), 4.81 (1H, dd, OCH$_2$), 5.16 (1H, m, CH).

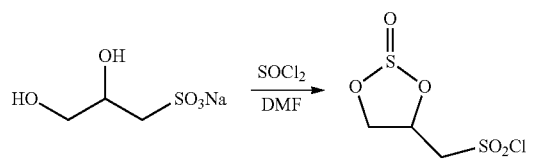

Example 2

Synthesis of 2-hydroxy-1,3-propanesultone

The Second Step, Reaction Scheme [III]

To 1,3,2-dioxathiolane-2-oxide-4-yl-methanesulfonyl chloride (4.21 g, 19.1 mmol) divided from the total amount thereof obtained in Example 1, 12 N hydrochloric acid (1.75 g, hydrogen chloride: 21.0 mmol, water: 62.2 mmol, produced by Wako Pure Chemical Industries, Ltd.) was added under ice-cooling, and the solution was stirred at room temperature for 30 minutes to promote the reaction. After completion of the reaction, ethyl acetate (50 mL) was added to the reaction solution, and then the solution was stirred. Subsequently, the organic layer was separated. After the separated organic layer was washed with water, the organic layer was concentrated, thereafter toluene was added to the concentrated residue. The crystal formed was filtered, and the resultant crystal was dried, to obtain 2-hydroxy-1,3-propanesultone (2.51 g, yield: 95%) relevant to the above-described general formula [1] as a white crystal. Measurement results of $^1$H-NMR are shown below.

$^1$H-NMR (400 MHz, acetone-d) δ (ppm): 3.26 (1H), 3.65 (1H), 4.33 (1H), 4.60 (1H), 4.99 (1H).

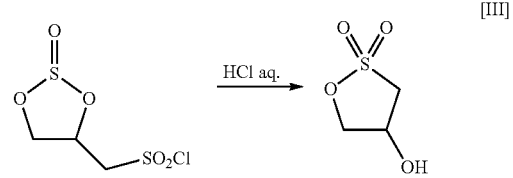 [SMILES: O=S1OCC(CS(=O)(=O)Cl)O1 ; "HCl aq." ; O=S1(=O)CC(O)CO1]

Example 3

Synthesis of 2-hydroxy-1,3-propanesultone

A Method where the First Step and the Second Step are Carried Out Continuously in One-Pot Reaction, Reaction Scheme [IV]

Sodium 2,3-dihydroxypropanesulfonate (4.0 g, 16.4 mmol, content: 73.3%) obtained according to Synthetic Example 1 was suspended in toluene (10 mL). Subsequently, N,N-dimethylformamide (DMF) (0.06 g, 0.823 mmol, produced by Wako Pure Chemical Industries, Ltd.) was added thereto, thereafter thionyl chloride (5.85 g, 49.2 mmol, produced by Wako Pure Chemical Industries, Ltd.) was added drop by drop, and the suspension was stirred at 65° C. for 7 hours to promote the reaction.

Subsequently, the reaction solution was cooled down to room temperature. Methanol (2.63 g, 82.0 mmol, produced by Wako Pure Chemical Industries, Ltd.) was added to the cooled solution, and the solution was stirred at room temperature for 2 hours to promote the reaction. After completion of the reaction, the reaction solution was concentrated under reduced pressure, and ethyl acetate (50 mL) and water (30 mL) were added to the resultant concentrated residue, and then the solution was stirred. Subsequently, the organic layer was separated. After separated organic layer was washed with water, the organic layer was concentrated, thereafter toluene was added to the concentrated residue. The crystal formed was filtered, and the resultant crystal was dried, to obtain 2-hydroxy-1,3-propanesultone (2.20 g, yield: 97%) relevant to the above-described general formula [1] as a white crystal.

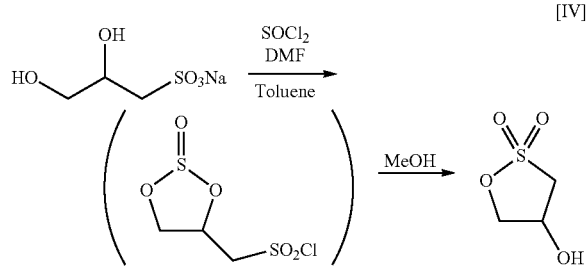

Example 4

Synthesis of 1,3-propenesultone

The Third Step, Reaction Scheme [V]

2-Hydroxy-1,3-propanesultone (1.70 g, 12.3 mmol) obtained according to Example 3 was dissolved in ethyl acetate (12 mL), and thereafter triethylamine ($Et_3N$) (2.99 g, 29.5 mmol, produced by Wako Pure Chemical Industries, Ltd.) and methanesulfonyl chloride (MsCl) (1.69 g, 14.7 mmol, produced by Wako Pure Chemical Industries, Ltd.) were added thereto under ice-cooling. The solution was stirred at −20° C. to 10° C. for 4 hours to promote the reaction. After completion of the reaction, water (12 mL) was added to the reaction solution, and then the solution was stirred. Subsequently, the organic layer was separated. After the separated organic layer was washed with water, the organic layer was concentrated, thereafter toluene was added to the concentrated residue. The crystal formed was filtered, and the resultant crystal was dried, to obtain 1,3-propenesultone (1.39 g, yield: 94%) relevant to the above-described general formula [4] as a white crystal. Measurement results of $^1$H-NMR are shown below.

$^1$H-NMR (400 MHz, $CDCl_3$) δ (ppm): 5.12 (1H), 6.81 (1H), 7.00 (1H).

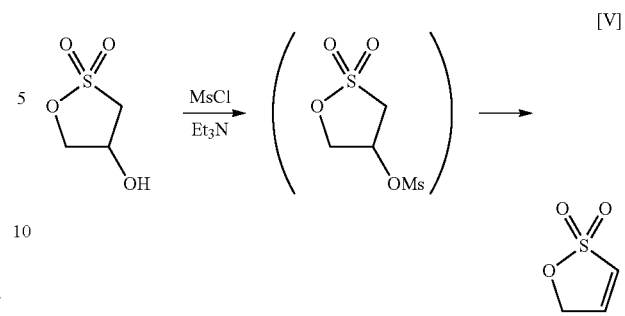

Example 5

Synthesis of 2-acetoxy-1,3-propanesultone

A Step to Obtain the Compound Represented by the General Formula [5] from the Compound Represented by the General Formula [1'] in the Third Step, Reaction Scheme [VI]

2-Hydroxy-1,3-propanesultone (1.49 g, 10.8 mmol) obtained according to Example 3 was dissolved in ethyl acetate (10 mL), and thereafter acetic anhydride ($Ac_2O$) (1.66 g, 16.2 mmol, produced by Wako Pure Chemical Industries, Ltd.) was added thereto. The solution was stirred at room temperature for 1 hour to promote the reaction. After completion of the reaction, water (10 mL) was added to the reaction solution, and then the solution was stirred. Subsequently, the organic layer was separated. After the separated organic layer was washed with saturated sodium bicarbonate aqueous solution and water sequentially, the organic layer was concentrated, to obtain 2-acetoxy-1,3-propanesultone (1.91 g, yield: 98%) relevant to the above-described general formula [5] as a brown oil. Measurement results of $^1$H-NMR are shown below.

$^1$H-NMR (400 MHz, $CDCl_3$) δ (ppm): 2.15 (3H), 3.35 (1H), 3.62 (1H), 4.47 (1H), 4.64 (1H), 5.61 (1H).

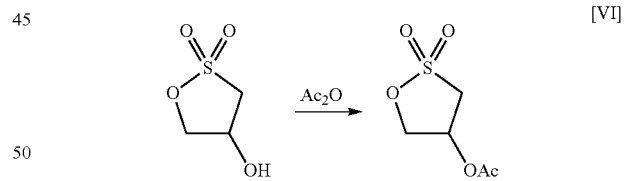

Example 6

Synthesis of 1,3-propenesultone

A Step to Obtain the Compound Represented by the General Formula [4] from the Compound Represented by the General Formula [5] in the Third Step, Reaction Scheme [VII]

2-Acetoxy-1,3-propanesultone (0.50 g, 2.78 mmol) divided from the total amount thereof obtained in Example 5 was dissolved in ethyl acetate (5 mL), and thereafter a solution of potassium carbonate (0.23 g, 1.66 mmol, produced by Wako Pure Chemical Industries, Ltd.) in water (5 mL) was added thereto. The solution was stirred at 40° C. for 12 hours to promote the reaction. After completion of the reaction, the reaction solution was washed with water, and then the organic layer was separated. After the separated organic layer was concentrated, to obtain 1,3-propenesultone (0.22 g, yield: 66%) relevant to the above-described general formula [4] as a white crystal.

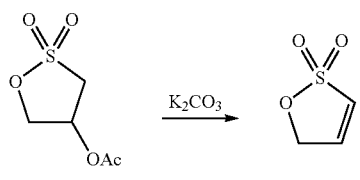

[VII]

Example 7

Synthesis of 1,3-propenesultone

A Method where the First, the Second and the Third Steps are Carried Out Continuously in One-Pot Reaction, Reaction Scheme [VIII]

Sodium 2,3-dihydroroxypropanesulfonate (4.0 g, 16.4 mmol, content: 73.3%) obtained according to Synthetic Example 1 was suspended in toluene (10 mL). Subsequently, N,N-dimethylformamide (DMF) (0.06 g, 0.823 mmol, produced by Wako Pure Chemical Industries, Ltd.) was added thereto, thereafter thionyl chloride (5.85 g, 49.2 mmol, produced by Wako Pure Chemical Industries, Ltd.) was added drop by drop, and the suspension was stirred at 65° C. for 7 hours to promote the reaction.

Subsequently, the reaction solution was cooled down to room temperature. Methanol (1.57 g, 49.2 mmol, produced by Wako Pure Chemical Industries, Ltd.) was added to the cooled solution, and the solution was stirred at room temperature for 2 hours to promote the reaction.

Subsequently, acetic anhydride (Ac$_2$O) (3.35 g, 32.8 mmol, produced by Wako Pure Chemical Industries, Ltd.) was added to the reaction solution, and the solution was stirred at room temperature for 1 hour to promote the reaction.

After completion of the reaction, water (15 mL) was added to the reaction solution, and then the solution was stirred. Subsequently, the organic layer was separated. A solution of potassium carbonate (3.40 g, 24.6 mmol, produced by Wako Pure Chemical Industries, Ltd.) dissolved in water (15 mL) was further added to the separated organic layer. The solution was stirred at 40° C. for 12 hours to promote the reaction. After completion of the reaction, the reaction solution was washed with water, and then the organic layer was separated. After the separated organic layer was concentrated, to obtain 1,3-propenesultone (1.18 g, yield: 60%) relevant to the above-described general formula [4] as a white crystal.

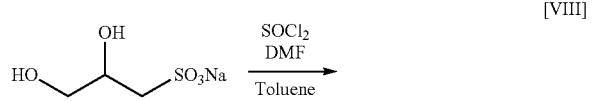

[VIII]

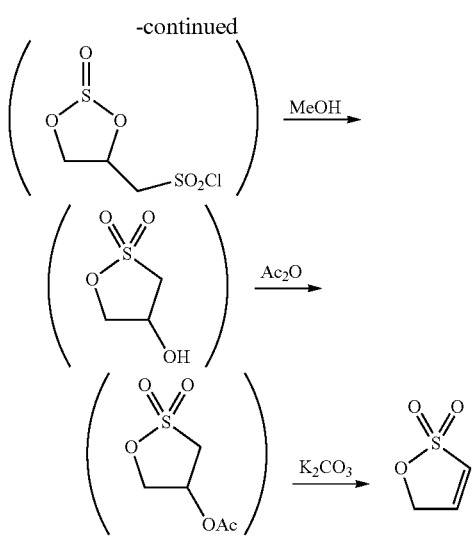

From the results of Examples 1 to 7, it was found that the desired hydroxysultone represented by the general formula [1] and the unsaturated sultone represented by the general formula [4] could be obtained in high yield by using the diol represented by the general formula [2] as a raw material through the cyclic sulfite represented by the general formula [3] as a synthetic intermediate. In addition, it was also found that these reactions could be carried out continuously in one-pot reaction, and that the production method of the present invention was very effective method also in efficiency because the desired compound could be obtained more efficiently by carrying out these reactions continuously.

INDUSTRIAL APPLICABILITY

The production method of the present invention can realize stable and efficient production in a commercial scale and the like of a cyclic sulfonic acid ester (sultone), which is useful, for example, as an additive to non-aqueous electrolyte in a lithium ion secondary battery or the like.

What is claimed is:
1. A compound represented by the formula [5]:

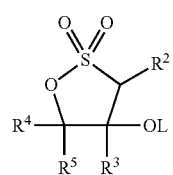

[5]

wherein R2, R3, R4 and R5 represent each independently a hydrogen atom or a C1-3 alkyl group, and L represents a C1-6 alkylsulfonyl group which is optionally substituted by a halogen atom, a C6-10 arylsulfonyl group which is optionally substituted by a halogen atom, a C6-10 arylsulfonyl group, a C2-7 alkylcarbonyl group which is optionally substituted by a halogen atom, or a C7-11 arylcarbonyl group.

2. The compound according to claim 1, wherein L is a C2-7 alkylcarbonyl group which is optionally substituted by a halogen atom, or a C7-11 arylcarbonyl group.

3. The compound according to claim 1, wherein L is a C2-7 alkylcarbonyl group which is optionally substituted by a halogen atom.

4. The compound according to claim 1, wherein L is a C2-7 alkylcarbonyl group.

5. The compound according to claim 1, wherein L is an acetyl group.

6. The compound according to claim 1, wherein $R^2$, $R^3$, $R^4$ and $R^5$ are a hydrogen atom.

7. The compound according to claim 1, wherein the compound represented by the formula [5] is 2-acetoxy-1,3-propanesultone.

* * * * *